(12) United States Patent
Ibrahim et al.

(10) Patent No.: US 8,082,040 B2
(45) Date of Patent: Dec. 20, 2011

(54) MULTI-ELECTRODE COCHLEAR IMPLANT SYSTEM WITH DISTRIBUTED ELECTRONICS

(75) Inventors: Ibrahim Hanna Ibrahim, North Ryde (AU); John L. Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 179 days.

(21) Appl. No.: 12/349,433

(22) Filed: Jan. 6, 2009

(65) Prior Publication Data

US 2009/0118795 A1 May 7, 2009

Related U.S. Application Data

(63) Continuation of application No. 10/481,209, filed as application No. PCT/AU02/00835 on Jun. 28, 2002, now abandoned.

(30) Foreign Application Priority Data

Jun. 29, 2001 (AU) ...................................... PR6048

(51) Int. Cl.
*A61F 2/18* (2006.01)

(52) U.S. Cl. .............. 607/57; 607/55; 607/56; 607/115; 607/116; 607/137

(58) Field of Classification Search .............. 607/55–57, 607/115–116, 137
See application file for complete search history.

(56) References Cited

U.S. PATENT DOCUMENTS

| | | | |
|---|---|---|---|
| 4,267,410 A | * | 5/1981 | Forster et al. ................... 607/57 |
| 4,441,202 A | | 4/1984 | Tong et al. |
| 4,515,158 A | | 5/1985 | Patrick et al. |
| 4,532,930 A | | 8/1985 | Crosby et al. |
| 4,611,596 A | | 9/1986 | Wasserman |
| 4,617,913 A | | 10/1986 | Eddington |
| 4,847,617 A | | 7/1989 | Silvian |
| 5,038,781 A | | 8/1991 | Lynch |
| 5,046,242 A | | 9/1991 | Kuzma |
| 5,271,397 A | | 12/1993 | Seligman et al. |
| 5,274,711 A | | 12/1993 | Rutledge et al. |
| 5,403,262 A | | 4/1995 | Gooch |
| 5,412,748 A | | 5/1995 | Furuyama et al. |
| 5,531,787 A | | 7/1996 | Lesinski et al. |
| 5,571,148 A | | 11/1996 | Loeb et al. |

(Continued)

FOREIGN PATENT DOCUMENTS

AU 2005202733 1/2006

(Continued)

OTHER PUBLICATIONS

Supplementary European Search report for corresponding European application EP 02 73 4913.

(Continued)

*Primary Examiner* — Niketa Patel
*Assistant Examiner* — Rex R Holmes
(74) *Attorney, Agent, or Firm* — Kilpatrick, Townsend & Stockton, LLP.

(57) ABSTRACT

An implantable tissue-stimulating device comprising a carrier member having a plurality of electrodes mounted thereon, and at least one signal transmitting wire extending through at least a portion of the carrier member and adapted to transmit signals through the carrier member to and/or from the electrodes. The number of wires within the carrier member is less than the number of electrodes mounted thereon.

25 Claims, 8 Drawing Sheets

U.S. PATENT DOCUMENTS

| | | | |
|---|---|---|---|
| 5,601,617 | A | 2/1997 | Loeb et al. |
| 5,603,726 | A | 2/1997 | Schulman et al. |
| 5,609,616 | A | 3/1997 | Schulman et al. |
| 5,626,629 | A | 5/1997 | Faltys et al. |
| 5,649,970 | A | 7/1997 | Loeb et al. |
| 5,653,742 | A | 8/1997 | Parker et al. |
| 5,687,282 | A | 11/1997 | Kerkhof |
| 5,749,912 | A | 5/1998 | Zhang et al. |
| 5,776,179 | A | 7/1998 | Ren et al. |
| 5,786,439 | A | 7/1998 | Van Antwerp et al. |
| 5,824,022 | A | 10/1998 | Zilberman et al. |
| 5,833,714 | A | 11/1998 | Loeb |
| 5,853,424 | A | 12/1998 | Rise |
| 5,895,416 | A | 4/1999 | Barreras, Sr. et al. |
| 5,909,497 | A | 6/1999 | Alexandrescu |
| 6,115,478 | A | 9/2000 | Schneider |
| 6,116,413 | A | 9/2000 | Tabor et al. |
| 6,119,044 | A | 9/2000 | Kuzma |
| 6,161,046 | A | 12/2000 | Maniglia et al. |
| 6,198,971 | B1 | 3/2001 | Leysieffer |
| 6,230,057 | B1 | 5/2001 | Chow et al. |
| 6,304,786 | B1 | 10/2001 | Heil, Jr. et al. |
| 6,304,787 | B1 | 10/2001 | Kuzma et al. |
| 6,321,126 | B1 | 11/2001 | Kuzma |
| 6,334,072 | B1 | 12/2001 | Leysieffer |
| 6,354,299 | B1 | 3/2002 | Fischell et al. |
| 6,355,064 | B1 | 3/2002 | Peeters et al. |
| 6,366,863 | B1 | 4/2002 | Bye et al. |
| 6,421,569 | B1 | 7/2002 | Treaba et al. |
| 6,463,328 | B1 | 10/2002 | John |
| 6,497,729 | B1 | 12/2002 | Moussy et al. |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,594,525 | B1 | 7/2003 | Zierhofer |
| 6,697,674 | B2 | 2/2004 | Leysieffer |
| 6,751,505 | B1 | 6/2004 | Van Den Honert et al. |
| 6,778,040 | B2 | 8/2004 | Kim |
| 6,778,858 | B1 | 8/2004 | Peeters |
| 6,826,430 | B2 * | 11/2004 | Faltys et al. .......... 607/137 |
| 6,879,693 | B2 | 4/2005 | Miller |
| 6,916,291 | B2 | 7/2005 | Givens et al. |
| 7,171,272 | B2 | 1/2007 | Blamey et al. |
| 7,181,297 | B1 | 2/2007 | Pluvinage et al. |
| 7,218,971 | B2 | 5/2007 | Heil, Jr. et al. |
| 7,251,530 | B1 | 7/2007 | Overstreet et al. |
| 7,272,446 | B2 | 9/2007 | Parker et al. |
| 7,317,944 | B1 | 1/2008 | Overstreet |
| 7,328,151 | B2 | 2/2008 | Muesch |
| 7,421,298 | B2 | 9/2008 | Daly |
| 2001/0031909 | A1 | 10/2001 | Faltys et al. |
| 2001/0050837 | A1 | 12/2001 | Stevenson et al. |
| 2002/0176584 | A1 | 11/2002 | Kates |
| 2003/0109903 | A1 | 6/2003 | Berrang et al. |
| 2003/0199950 | A1 | 10/2003 | Stolz et al. |
| 2003/0233133 | A1 | 12/2003 | Greenberg et al. |
| 2004/0098063 | A1 | 5/2004 | Goelz |
| 2004/0127968 | A1 | 7/2004 | Kuzma et al. |
| 2004/0147992 | A1 | 7/2004 | Bluger et al. |
| 2006/0004432 | A1 | 1/2006 | Parker et al. |
| 2006/0025833 | A1 | 2/2006 | Daly |
| 2007/0127745 | A1 | 6/2007 | Gibson et al. |
| 2008/0119910 | A1 | 5/2008 | Daly |
| 2009/0204177 | A1 | 8/2009 | Parker et al. |

FOREIGN PATENT DOCUMENTS

| | | |
|---|---|---|
| EP | 0247649 | 12/1987 |
| EP | 0282336 | 9/1988 |
| EP | 0124930 | 6/1990 |
| JP | 61001200 | 1/1986 |
| JP | 63242252 | 10/1988 |
| JP | 8501241 | 2/1996 |
| JP | 10508442 | 8/1998 |
| JP | 11513539 | 11/1999 |
| JP | 2000-508210 | 7/2000 |
| WO | WO-9324176 | 12/1993 |
| WO | WO-9501709 | 1/1995 |
| WO | WO-9612383 | 4/1996 |
| WO | WO-9626673 | 9/1996 |
| WO | WO-9709863 | 3/1997 |
| WO | WO-9738653 | 10/1997 |
| WO | WO-9743871 | 11/1997 |
| WO | WO-9748447 | 12/1997 |
| WO | WO-9965276 | 12/1999 |
| WO | WO 00/64529 A1 | 11/2000 |
| WO | WO-0103622 | 1/2001 |
| WO | WO-0119304 | 3/2001 |
| WO | WO-0199470 | 12/2001 |
| WO | WO-0217679 | 2/2002 |
| WO | WO 02/089907 A1 | 11/2002 |

OTHER PUBLICATIONS

International Search report for PCT/AU02/00835, dated Jul. 17, 2002.

International Preliminary Examination Report for PCT/AU02/00835, dated Sep. 25, 2003.

Corresponding Australian Priority Application Search Report PR6048, dated Jul. 31, 2001.

Office action of corresponding Japanese Application No. 2003-509823 dated Jan. 15, 2008 and English translation thereof, 8pp.

Sep. 15, 2010, Communication Pursuant to Article 94(3) EPC issued in EP Application No. 02734913.3.

CA Examiner's report, CA Application No. 2,419,321, mailed May 29, 2007.

CA Examiner's report, CA Application No. 2,419,321, mailed Dec. 10, 2008.

Specialty Coating Systems: Rubber/Silicone, *Specialty Coating Systems, (Webpage)*, www.scscoatings.com/1_parylene_applications/rubber-silicone.cfm, accessed via Internet Archive Wayback Machine (archive.org), available Nov. 24, 2005 (based on records of Internet Archive).

European Search Report, EP Application No. 01959971, mailed Aug. 11, 2005.

First European Examiner's Report, EP 01959971.1 mailed Nov. 23, 2005.

Office Action, U.S. Appl. No. 11/192,014, mailed Jun. 25, 2008.

Office Action, U.S. Appl. No. 11/192,014, mailed Mar. 20, 2009.

Notice of Allowance, U.S. Appl. No. 11/219,823, mailed Feb. 27, 2008.

Notice of Allowance, U.S. Appl. No. 11/219,823, mailed Oct. 4, 2007.

Notice of Reasons for Rejection, JP2002-561453, mailed Jun. 16, 2009.

Office Action, JP 2003-509823, mailed Oct. 28, 2008.

Office Action, JP 2003-509823, mailed Aug. 19, 2008.

Office Action, JP 2003-509823, mailed Jan. 15, 2008.

Abbas, et al., "Electrically Evoked Compound Action Potentiais Recorded from Subjects Who Use the Nucieus C12M Device", Gantz et al. *Seventh Symposium On Cochlear Implants in Children Ann. Otol. Rhinol. Laryngol. Suppl*, 185 Dec. 2000, 185, 6-9.

Examiner's First Report, AU2002311095, mailed Sep. 26, 2006.

Notice of Acceptance AU2002311095, mailed Jun. 16, 2008.

Baumgarte, et al., "A Nonlinear Psychoacoustic Model Applied to the ISO MPEG Layer 3-coder", *Proceedings of the 99th Convention Aud. Eng. Soc., New York . Institut for Theoretische Nachrichtentechnik und Informationsverarbeitung, Universitat Hannover. Germany* Oct. 1995.

Cohen, et al., "Spatial spread of neural excitation in cochlear implant recipients:—comparison of improved ECAP method and psychophysical forward masking", *Hearing Research* May 2003, vol. 179, pp. 72-87.

Cohen, et al., "Spatial spread of neural excitation: comparison of compound action potential and forward-masking data in cochlear implant recipients", *International Journal of Audiology* 2004, vol. 43, pp. 346-355.

Edler, et al., "ASAC Analaysis/Synthesis Audio Codec for Very Low Bit rates", *Proceedings of the 100th Cony. Aud. Eng. Soc. Institit for theoretische Nachrichtentechnik und Informationsverarbeitung, Universitat Hannover*, Germany May 1996.

Miller, et al., "An Improved Method of Reducing Stimulus Artifact in the Electrically Evoked whole Nerve Potential", *Ear & Hearing* Aug. 2000, 21(4): 280-290.

Nogueira, et al., "A Psychoacoustic 'NofM'-Type Speech Coding Strategy for Cochlear Implants", *EURASIP journal on Applied Signal Processing* 2005, 3044-3059.

International Preliminary Examination Report, PCT/AU2001/01032, mailed Apr. 2, 2002.

International Search Report, PCT/AU2001/01032, mailed Oct. 5, 2001.

* cited by examiner

SECTION A-A

MULTI-ELECTRODE COCHLEAR IMPLANT SYSTEM WITH DISTRIBUTED ELECTRONICS

CROSS-REFERENCE TO RELATED APPLICATIONS

This application is a continuation of U.S. patent application Ser. No. 10/481,209, filed on Aug. 23, 2004, now abandoned which is a National Phase Patent Application of International Application Number PCT/AU02/00835, filed on Jun. 28, 2002, which claims the priority of Australian Patent Application No. PR 6048, filed on Jun. 29, 2001. The contents of which are hereby incorporated by reference.

FIELD OF THE INVENTION

The present invention relates to a tissue-stimulating prosthesis and, in particular, to an implantable tissue-stimulating prosthesis, such as an electrode array for a cochlear implant-type auditory prosthesis.

BACKGROUND OF THE INVENTION

Cochlear implants have been developed to assist people who are profoundly deaf or severely hearing impaired, by enabling them to experience hearing sensation representative of the natural hearing sensation. In most of these cases, the individuals have an absence of or destruction of the hair cells in the cochlea which naturally transduce acoustic signals into nerve impulses which are interpreted by the brain as sound. The cochlear implant therefore bypasses the hair cells to directly deliver electrical stimulation to the auditory nerves with this electrical stimulation being representative of the sound.

Cochlear implants have traditionally consisted of two parts, an external speech processor unit and an implanted receiver/stimulator unit. The external speech processor unit has normally been worn or carried on the body of the user and its main purpose has been to detect sound with a microphone and convert the detected sound into a coded signal through an appropriate speech processing strategy.

This coded signal is then sent to the receiver/stimulator unit which is normally implanted in the mastoid bone of the user, via a transcutaneous radio frequency (RF) link. The receiver/stimulator unit includes a circuit that processes this coded signal and outputs a series of stimulation sequences. These sequences are transmitted to appropriate electrodes of an electrode array by respective electrically conducting wires. The array is positioned proximal to the modiolus of the cochlea such that an electrical stimulus output by the electrodes is then applied to the auditory nerve.

As the electrode array is typically surgically implanted within the scala tympani of the cochlea of the recipient, the dimensions of the array and the manner of its insertion must be such so as to avoid damage to the sensitive structures of the cochlea. The dimensions and spiral shape of the cochlea also limit the maximum dimensions, particularly the diameter, and the stiffness of any array used as part of a cochlear implant.

In existing designs, this has limited the number of electrically conducting electrodes that can be incorporated into the array, due in the main to limitations imposed on the number of wires that can extend through the array to the electrodes. Traditional electrode array designs have required one or more conductive wires to be connected to each electrode and as such for an array having, for example 22 electrodes, the minimum number of wires required would be 22. With an increased understanding of the tonotopic nature and behavior of the cochlea, the benefits of providing an increased number of stimulating electrodes within the cochlea to stimulate more discrete sites within the cochlea are now being realized. However, it has been demonstrated that increasing the number of wires in conjunction with an increased number of electrodes unacceptably increases the dimensions and stiffness of the array. Merely reducing the diameter of the wires, in order to keep the overall dimensions unchanged, leads to an unacceptable increase in lead resistance. As a result, this limitation on the number of leads, and hence electrodes, limits the scale and type of electrical stimulations that can be applied to the auditory nerve by the electrode array.

The present invention provides a solution to this problem by allowing an increase in the number of individual electrodes of an electrode array of a cochlear implant in comparison to known arrays while still allowing the array to be readily inserted within a implantee's cochlea.

Further to this, the present invention in combination with new methods of manufacturing electrode arrays as described in the Applicant's co-pending International Patent Application PCT/AU02/00575, provides for significant improvements in the size and design of intra-cochlear electrode arrays than has previously been the case.

Any discussion of documents, acts, materials, devices, articles or the like which has been included In the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is an implantable tissue-stimulating device comprising a carrier member having a plurality of electrode elements mounted thereon, and at least one signal transmitting means extending through at least a portion of the carrier member and adapted to transmit signals through the carrier member to and/or from said plurality of electrode elements, wherein the number of transmitting means within the carrier member is less than the number of electrode elements mounted thereon.

According to a second aspect, the present invention is an implantable tissue-stimulating device comprising a carrier member having a plurality of electrode elements mounted thereon, at least one of the electrode elements having associated signal processing circuitry embedded within the carrier member proximate thereto.

In a preferred embodiment, the tissue-stimulating device of both aspects can comprise an implantable component of a cochlear implant device. While having broader application, the present invention will be defined for the purposes of the present application with reference to a cochlear implant. For the purposes of the present specification, the cochlear implant is defined as including a receiver/stimulator circuit which is implanted in the mastoid bone of the implantee. The receiver/stimulator unit includes a circuit that processes a coded signal transmitted transcutaneously from an external component and outputs a series of signals through the carrier member to the electrodes and/or the embedded circuitry of the carrier member. While a typical cochlear implant will include an external component including a microphone and speech processor, it will be appreciated that the cochlear implant could be fully implantable within the implantee.

In a preferred embodiment, the plurality of electrode elements define a longitudinal array of elements. In a further embodiment, the electrode elements each have a respective contact face exposed along a first, preferably longitudinal, side of the carrier member. In one embodiment, the contact faces can be equally spaced along the carrier member. In another embodiment, the spacing between respective pairs of contact faces can vary. In another embodiment, respective pairs of electrodes can be adapted to provide bipolar stimulation. In another embodiment, the electrode or electrodes can provide monopolar stimulation or common ground stimulation to the auditory nerve in the cochlea.

The electrode elements can be formed of a biocompatible material, such as platinum.

In a further embodiment of the first aspect, the signal transmitting means can comprise an electrically conducting wire or wires. In one embodiment, the wire or wires can also be formed of a biocompatible electrically conducting material, such as platinum. In one embodiment, the device includes at least five signal transmitting means for all of the electrodes in the carrier member This is in contrast to present known designs which normally have at least one wire for each of the electrodes of the array, e.g. at least 32 wires for 32 electrodes.

The five signal transmitting means can include a clock line, a data line, a first stimulation line, a second stimulation line, and a common ground line.

In a further embodiment of the first aspect and in the second aspect, each electrode supported by the carrier member has associated electronic circuitry positioned proximate thereto within the carrier member. The circuitry can be associated with one or more electrodes. This circuitry can be positioned immediately adjacent the electrode. In another embodiment, the electrode and its associated circuitry are integrated on a common substrate to form an integrated circuit. The circuitry and substrate are each preferably constructed to be biocompatible, with preferably no metal interlayers being utilized. Instead, polysilicon is preferably used to provide low impedance pathways within the circuitry.

The electronic circuitry can include a power rectifier, a data decoder, a control circuit, and/or an output switch.

DC power for its associated electrode is preferably produced by the power rectifier by rectifying an AC power source provided to the power rectifier. The AC power is preferably provided on two signal transmitting means extending through the carrier member from the implanted receiver/stimulator circuit The two signal transmitting means can comprise the data line and the clock line as defined above.

The data and clock lines are preferably capacitively coupled to the associated electronic circuitry of each of the electrodes in the carrier member using respective input pads.

The data and clock lines are also preferably coupled to the electrode via small coupling capacitors formed under, and including, the data and clock bond pads.

The circuitry preferably includes a ground pad. The ground pad is preferably bonded to a platinum wire that connects to the ground of the receiver/stimulator circuit, i.e. the common ground line. It is also preferably connected to the common ground of the electronic circuit of the electrode.

The stimulus pads of the integrated substrate are preferably constructed using standard CMOS bond pad design. These pads preferably do not require protection diodes.

The data decoder preferably demodulates data and power signals transmitted from the receiver/stimulator circuit, extracts the data and decodes it to obtain the stimulation and telemetry control parameters. Each electrode data decoder preferably determines whether its associated electrode is required to output an electrical stimulation. By devolving this decoding step to circuitry embedded with the respective electrodes, the number of electrical connections between the electrodes and the receiver/stimulator passing through the carrier member can be reduced.

The control circuit is preferably used to configure the electrode output in accordance with the stimulus and telemetry data decoded by the data decoder.

The output switch (transmission gate) preferably directs the stimulation current to the selected electrode and/or connects the selected electrode to a telemetry measurement circuit. Each output switch also preferably controls the shorting of the electrodes during an inter-frame period, or to open the electrode outputs during voltage and neural response telemetry. The platinum electrode is preferably directly bonded to the drains of transistors within the output switch.

In one embodiment, the wires forming the respective signal transmitting means extend from at least the proximal end of the carrier member for a length through the carrier member that includes the electrodes.

The wires are preferably electrically insulated. A ribbon wire can be used to provide the signal transmitting means. The electrical insulation can comprise parylene. Where necessary, the insulation can be ablated using excimer laser ablation. The insulation is preferably ablated at fixed intervals corresponding to the positions of the input pads within the carrier member of each embedded circuit.

In one embodiment, the wire can be gap welded to the input pads using an appropriate gap welder.

In another embodiment, the input pads can be fabricated to form insertion displacement connectors. The connector can be fabricated by micromachining a cavity having a plurality of sharp tines formed in the surface thereof. On pushing the wire into this cavity, the sharp fines can pierce the insulation of the wire and so make electrical connection with the wire.

The carrier member can be formed by molding a suitable biocompatible polymer around the wires, circuitry and electrodes.

The carrier member can be formed to have a first configuration selected to allow said member to be inserted into an implantee's body and at least a second configuration wherein said carrier member is adapted to apply a preselected tissue stimulation with the electrodes.

A stiffening element having a configuration selected for biasing said carrier member into said first configuration can pass through at least a portion of the carrier member. The stiffening element can be a metallic stylet disposed in a lumen passing through the carrier member.

In a preferred embodiment, the second configuration of the carrier member is curved. More preferably, the carrier member adopts a spiral configuration when in the second configuration.

In a preferred embodiment, the first configuration is preferably substantially straight. More preferably, the first configuration is straight.

In a preferred embodiment, the carrier member is formed from a suitable biocompatible material. In one embodiment, the material can be a silicone, such as Silastic MDX 4-4210. In another embodiment, the carrier member can be formed from a polyurethane.

In a preferred embodiment, the receiver/stimulator circuit of the cochlear implant is electrically connected to the data and clock lines. It is also preferably electrically connected to and drives four output stimulation lines. Two of these lines are preferably connected to two extra-cochlear electrodes. The other two lines, hereinafter called "stim 1" and "stim 2", extend through the carrier member and are connected to the respective input pads of the embedded circuits.

Each of the four lines can be connected, under the control of the receiver/stimulator circuit, to either VDD or to an on-chip stimulus current source.

The stimulation charge, delivered to the cochlea, is preferably balanced by using a two-phase balanced stimulation scheme. During the first phase, the active electrode is connected to the current source while the reference electrode is connected to VDD. This allows the current to flow from the reference electrode, through the cochlea and other tissue, to the active electrode. During the second phase, the electrode connections are reversed allowing equal, but opposite polarity, charge to flow through the cochlea. This preferably results in a balanced (zero average) charge flow through the stimulating electrodes and the human tissue.

Despite the above, precise charge balance may not be achievable in practice due to small timing errors or variation in electrode properties. To overcome this problem, the output transmission gates (switches) are preferably closed after the second stimulation phase, thereby connecting all intra-cochlea electrodes to stim 1 and stim 2 simultaneously. These electrodes can be connected to VDD via the output switches of the receiver/stimulator circuit. Depending on the desired shorting scheme, the extra-cochlear electrodes may also be shorted to VDD together with the intra-cochlea electrodes in order to simultaneously discharge any residual charge on all electrodes. The insertion of series capacitors with some, or all, of the four output lines of the receiver/stimulator circuit preferably guarantees the longer term charge balance of the system.

As discussed, the implant is preferably capable of three stimulation modes. Monopolar stimulation is obtained by selecting an extra-cochlear electrode and an intracochlear electrode as the stimulating electrodes. In this mode, the post-stimulating shorting must involve the extra-cochlea electrodes.

The bipolar stimulation is preferably achieved by selecting two intra-cochlear electrodes as the stimulating electrodes. The post-stimulation shorting, in this case, does not need to involve the extra-cochlear electrodes.

The Common Ground stimulation is obtained by selecting an intra-cochlea electrode as an active electrode (connected to stim 1), while all other intra-cochlea electrodes are connected in parallel to stim 2 by simultaneously closing their output switches (transmission gates) during the stimulus phases.

A telemetry circuit can reside in the receiver/stimulator circuit and be connected to the four output lines. This preferably enables the telemetry circuit to measure the voltage of any of the four lines with respect to an internal reference, or differentially between any two of the four lines.

Three telemetry functions are preferably available when using the system, namely Current Source Voltage Compliance Telemetry, Voltage Telemetry, and Neural Response Telemetry.

Current Source Voltage Compliance Telemetry is preferably used to measure the voltage across the stimulation current source of the receiver/stimulator circuit. This telemetry function returns one of two states indicating the voltage across the current source during stimulation. If the measured voltage falls below a design threshold, it may not then be sufficient to maintain the correct operation of the current source. This telemetry function is available for both monopolar and bipolar stimulation modes.

Electrode Voltage Telemetry is preferably used to measure the voltage of an intra-cochlea electrode during stimulation. When voltage telemetry is used to measure the voltage of the active electrode, it can then be used with either monopolar or bipolar stimulation modes. However, only monopolar stimulation can facilitate using Voltage telemetry to measure the voltage of a non-stimulating intra-cochlea electrode, where one of the two lines, stim 1 and stim 2, is used to carry the monopolar stimulation current while the other is used as a sense line to connect to the electrode to be measured.

Neural Response Telemetry can preferably be used to measure the evoked potential of the auditory nerve after stimulation. This is achieved in monopolar mode by using either stim 1 or stim 2 as a sense line for the neural response electrode. To reduce the stimulation artifacts, one of the extra-cochlea electrodes can be used as a stimulation reference electrode, while the other can be used as a reference electrode for the neural response measurement.

BRIEF DESCRIPTION OF THE DRAWINGS

By way of example only, a preferred mode of carrying out the invention is described with reference to the accompanying drawings, in which.

PREFERRED MODE OF CARRYING OUT THE INVENTION

While it is to be understood that the present invention has wider application, the invention will be hereinafter described with reference to its application in a cochlear implant.

Figure 11:
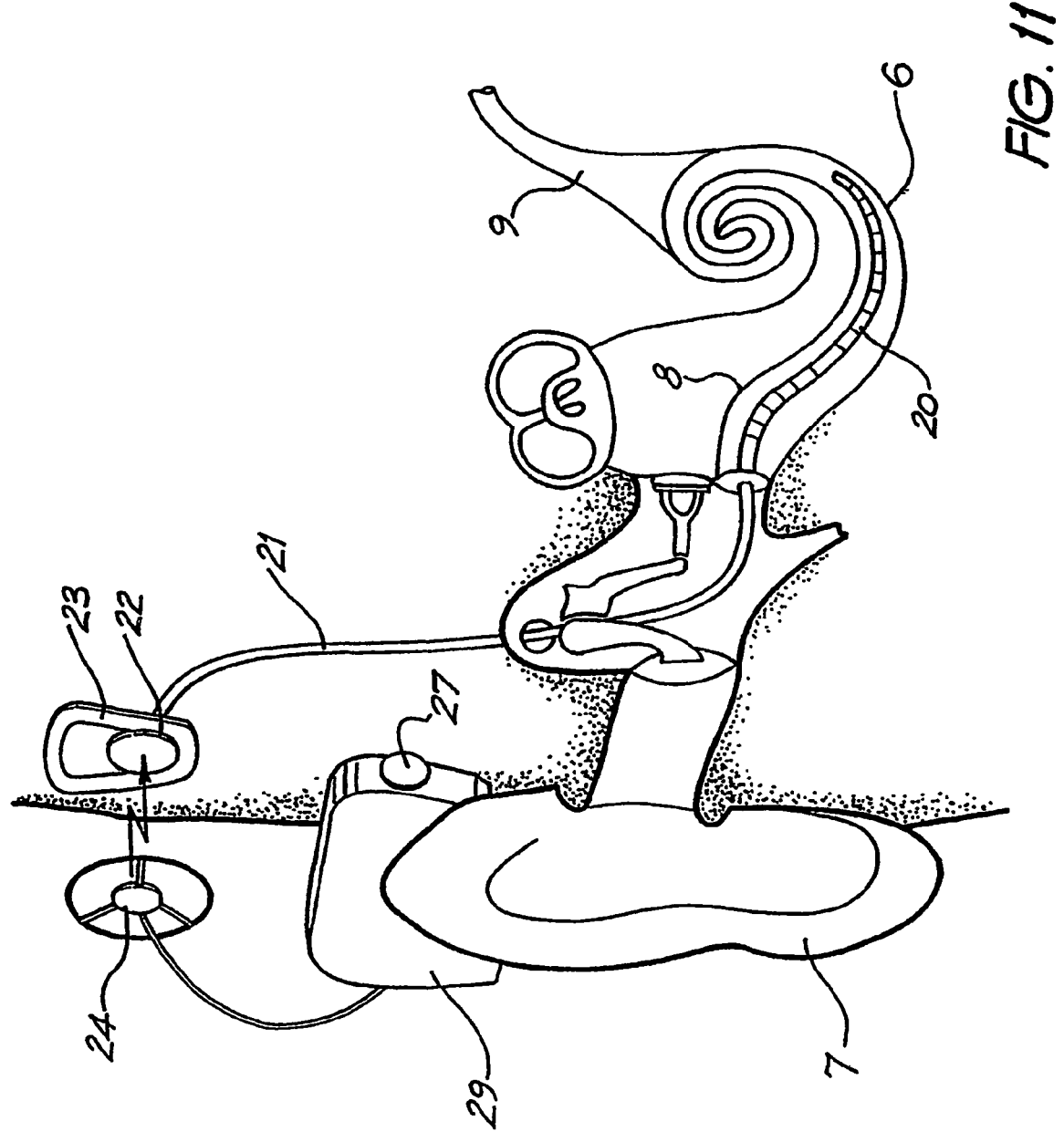
FIG. 11 is a simplified pictorial representation of a prior art cochlear implant system.

Before describing the features of the present invention, it is appropriate to briefly describe the construction of one type of known cochlear implant system with reference to FIG. 11.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 7. Alternative versions may be worn on the body or be totally implantable. In the depicted arrangement, a transmitter coil 24 receives signals from the speech processor 29 which in turn transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 6 and terminates in an electrode carrier 20. The signals thus received are applied by the electrodes of the carrier 20 to the basilar membrane 8 thereby stimulating the auditory nerve 9. The operation of such a device is described, for example, in U.S. Pat. No. 4,532,930.

Figure 10:
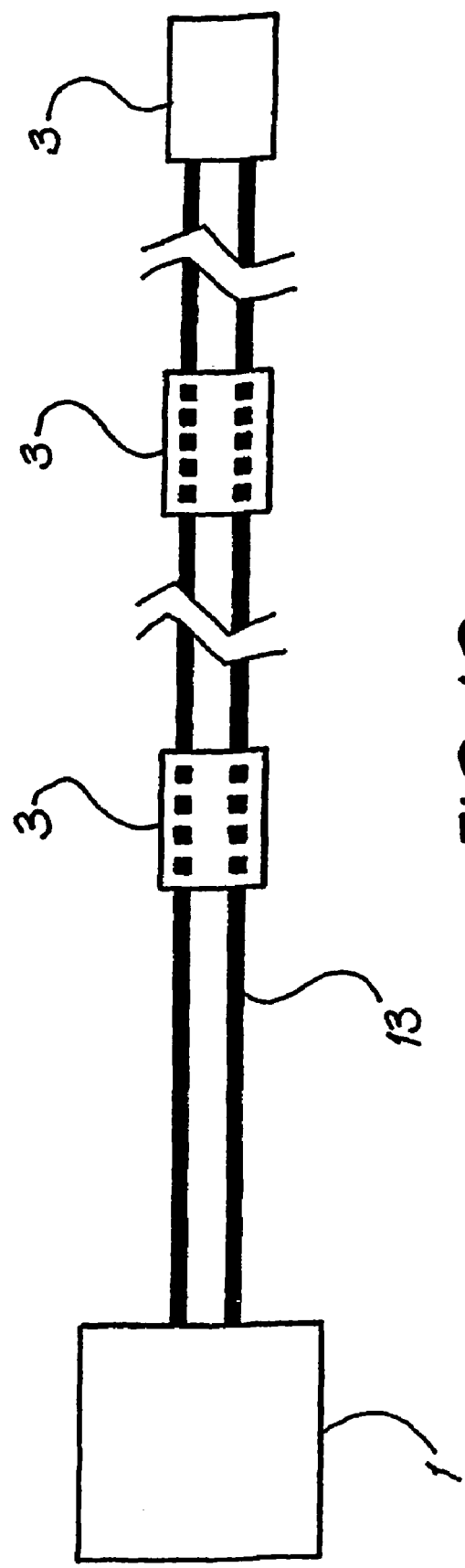
FIG. 10 is a schematic overview of the present invention.

A schematic overview of the present invention is shown in FIG. 10. In this overview, a centralized electronics package 1 is provided and can be considered to be the receiver and stimulator unit as described above. A number of stimulating sites 3 are shown which consist of a plurality of contact surfaces arranged so as to deliver stimulation to the desired tissue. In the present invention, each stimulation site will include embedded electronic circuitry as will be discussed in more detail below. Connecting each stimulation site 3 and the centralized electronics 1 are connecting wires or cables 13. The function of the connecting wires or cables 13 is to supply the power, stimulation site address and stimulation data etc issued from the centralized electronics 1, to be processed and delivered by the stimulation sites 3.

As can be appreciated by this simplified overview, with such an arrangement not only will the array containing the stimulation sites be able to include more stimulation sites, but due to the lack of wires required to connect to each stimulation site separately; the array will be more flexible and easily maneuverable. Further to this benefit, as the stimulation sites will contain electronics, the need to house all the electronics in the centralized electronics package 1 will be reduced, resulting in the size of the centralized electronics package 1 becoming smaller.

Figure 1:
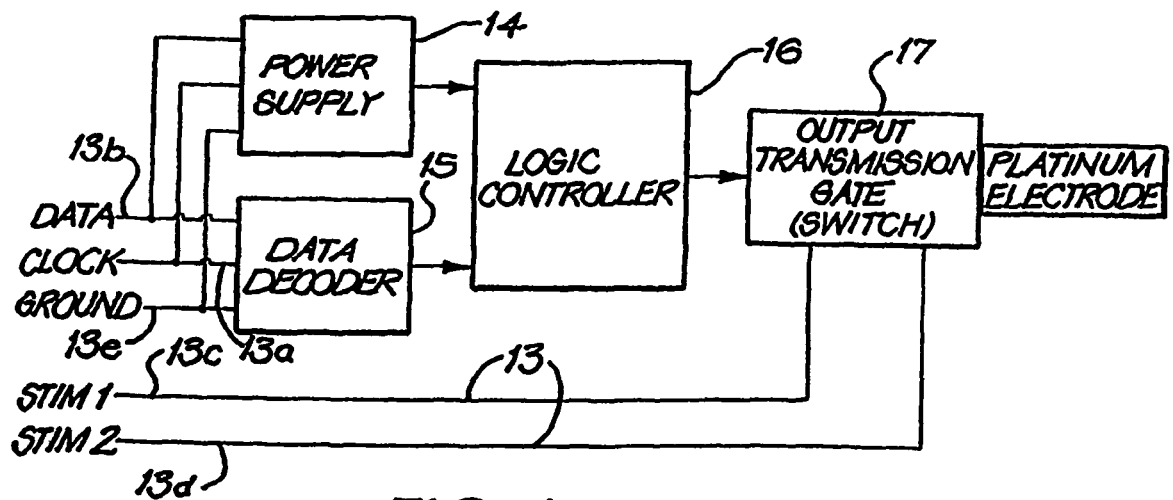
FIG. 1 is a block diagram of one embodiment of the embedded circuitry in a carrier member for an electrode.
Figure 2:
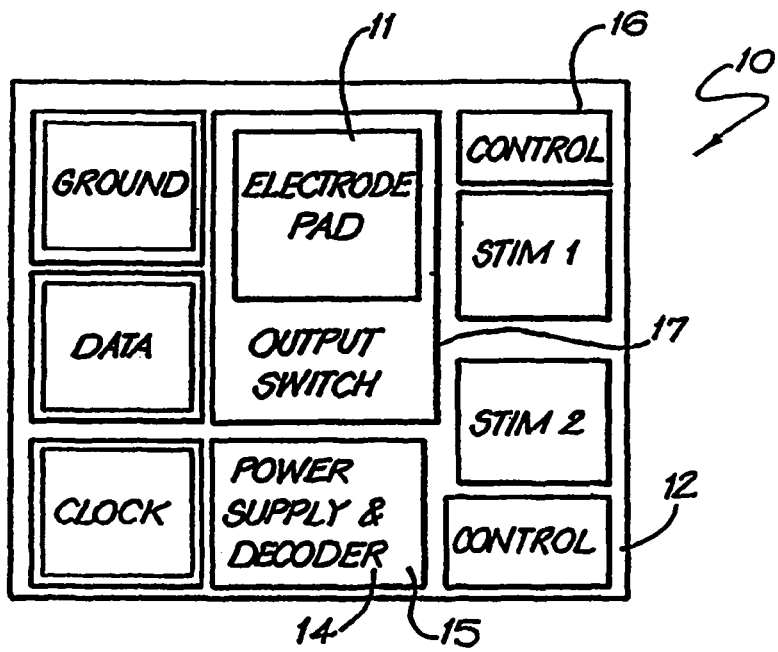
FIG. 2 is a plan view of the embedded circuitry.

One possible layout of the embedded circuitry 10 associated with an electrode 11 of a stimulation site 3 is depicted in FIG. 2. In the depicted embodiment, the circuitry is provided on a substrate 12 that is square in shape. In the depicted embodiment, the sides of the substrate 12 are 500 microns in length; with the bond pads for the circuits each being squares having side lengths of about 100 microns.

Figure 9A:
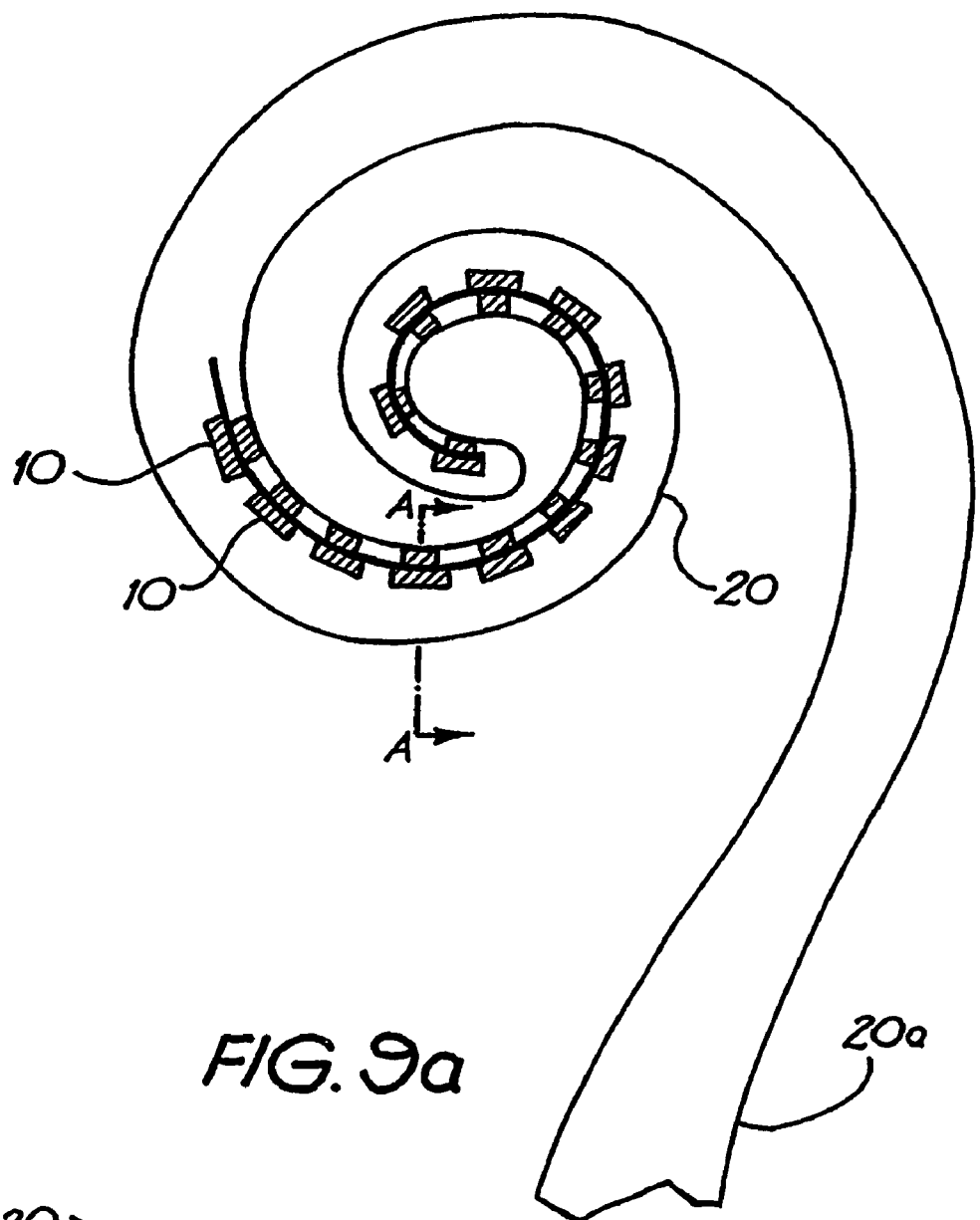
FIGS. 9a and 9b are views of one embodiment of a carrier member having an array of electrodes and associated embedded circuitry positioned therealong.
Figure 9B:
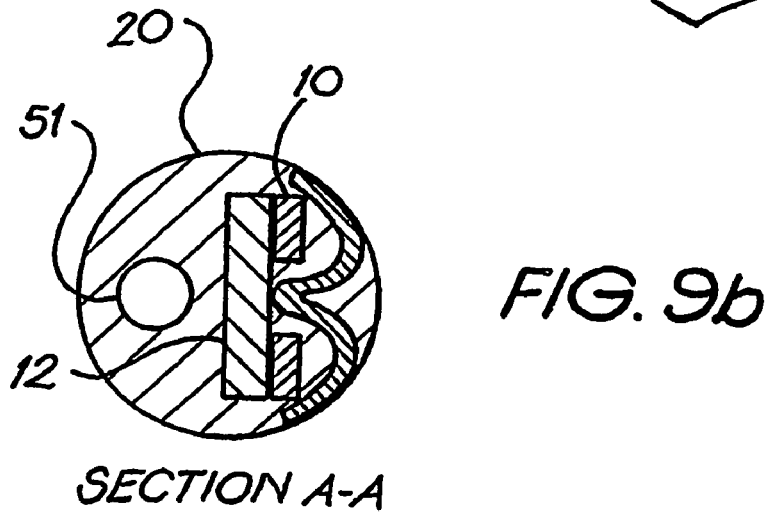

The depicted circuitry 10 is adapted to control the stimulation output by an associated platinum electrode 11 that is integrated on the substrate 12 supporting the remainder of the circuitry 10. A plurality of such embedded circuits with associated electrodes 11 are disposed along at least a portion of the length of the carrier 20 (see FIGS. 9a and 9b).

Extending through the carrier 20 from the receiver/stimulator 22 are at least five electrically conducting wires or cables 13. The wires 13 are formed from a biocompatible material, such as platinum.

The five wires include a clock line 13a, a data line 13b, a first stimulation line 13c, a second stimulation line 13d, and a common ground line 13e.

The electronic circuitry 10 for each electrode 11 includes a power rectifier 14, a data decoder 15, a control circuit 16, and an output switch 17.

DC power for its associated electrode 11 is produced by the power rectifier 14 which rectifies AC power provided to the rectifier 14 on the data line 13b and clock line 13a.

Figure 3:
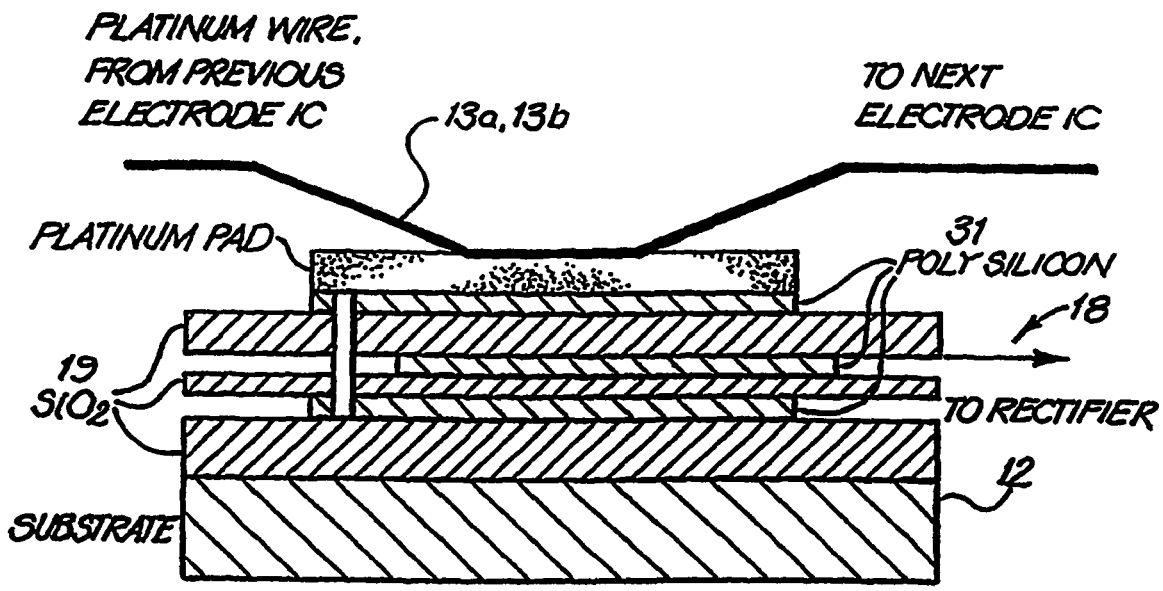
FIG. 3 is a cross-sectional view of the data and clock input pads of the is circuitry of FIG. 2.

The data line 13b and clock line 13a are capacitively coupled to the electronic circuitry 10 of each of the electrodes 11 in the carrier 20 using respective input pads 18, such as is depicted in FIG. 3. The data line 13b and clock line 13a are coupled to the circuitry 10 via small coupling capacitors formed under, and including, the data and clock bond pads. The pad structure 18 depicted in FIG. 2 is designed to allow the application of large AC voltages to the pad 18, up to the breakdown voltage of the silicon oxide layers 19 in the pad. The structure also maximizes the coupling capacitance to the rest of the circuitry 10. The pad 18 is comprised of multi-layer, inter-digitized, parallel connected polysilicon plates 31 to form a large coupling capacitance while keeping the surface area, and hence the capacitance to substrate, small. The capacitance to substrate forms a loss path in the pad 18, where voltage and current losses are incurred, and should be kept to a minimum value.

Figure 4:
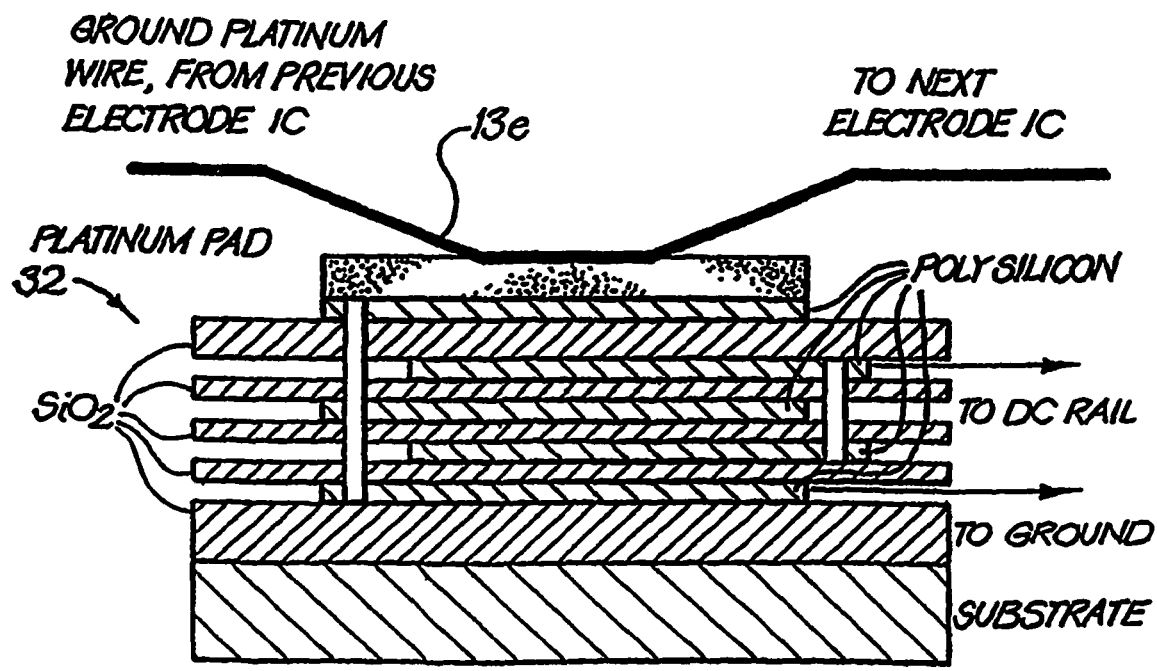
FIG. 4 is a cross-sectional view of the ground pad and power supply bypass capacitor of the circuitry of FIG. 2.

The depicted circuitry 10 also includes a ground pad 32, as depicted in FIG. 4. The ground pad 32 is bonded to the platinum wire 13e that connects to the ground of the receiver/stimulator circuit, i.e. the common ground line. It is also connected to the common ground of the electronic circuit of the electrode. The capacitor formed beneath the ground pad 32 is used as a power supply bypass capacitor.

The stimulus pads of the integrated substrate 12 are constructed using standard CMOS bond pad design. These pads do not require protection diodes as the output switches 17 are relatively large and have large parasitic diodes to the substrate 12. The capacitance from each stimulus pad to the substrate 12 is made relatively small by using a relatively thick underlying oxide layer. The stimulus current, connected to this pad is generated by the receiver/stimulator 22. The current waveform is made of two phases. Each phase carries equal, but opposite polarity, charges such that the average charge per stimulus frame is zero.

Figure 5:
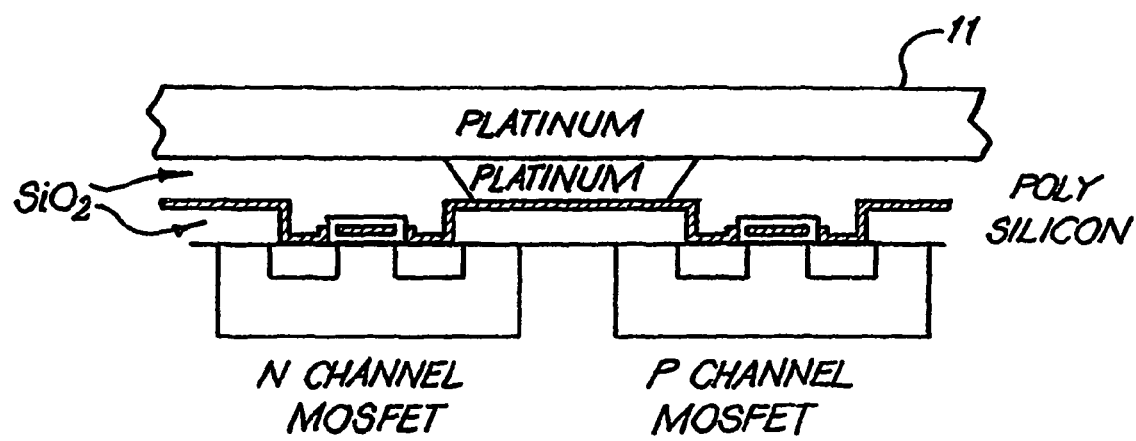
FIG. 5 is a cross-sectional view of the output switch and platinum electrode of the circuitry of FIG. 2.

The platinum output electrode 11 is directly bonded to the drain diffusions of the output transistors. The field oxide under the electrode area is made thick enough to reduce the field threshold modulation caused by the change in the electrode voltage during stimulation, as is depicted in FIG. 5.

The data decoder 15 demodulates data and power signals transmitted from the receiver/stimulator circuit 22, extracts the data and decodes it to obtain the stimulation and telemetry control parameters. Each electrode data decoder 15 determines whether its associated electrode 11 is required to output an electrical stimulation. By devolving this decoding step to embedded circuitry 10 with the respective electrodes 11, the number of electrical wires 13 between the electrodes 11 and the receiver/stimulator 22 passing through the carrier 20 are substantially reduced.

The control circuit 16 is used to configure the electrode output in accordance with the stimulus and telemetry data decoded by the data decoder 15.

The output switch (transmission gate) 17 directs the stimulation current to the selected electrode 11 and/or connects the selected electrode 11 to a telemetry measurement circuit. Each output switch 17 also controls the shorting of the electrodes 11 during an inter-frame period, or to open the electrode outputs during voltage and neural response telemetry. The platinum electrode 11 is directly bonded to the drains of the transistors of the output switch 17.

In the depicted embodiment, the wires 13 extend from receiver stimulator 22 and through the proximal end 20a of the carrier 20 to the respective circuits 10.

The depicted wires 13 are electrically insulated with parylene. During manufacture, this insulation can be ablated using excimer laser ablation. The insulation is preferably ablated at fixed intervals corresponding to the positions of the input pads 18 within the carrier 20 of each embedded circuit 10.

In another arrangement, the wires can be gap welded to the input pads 18 using an appropriate gap welder.

In yet another embodiment, the wires and the input pads can be made integrally using the method as described in PCT Patent Application No. PCT/AU02/00575, the contents of which is incorporated herein by reference.

Figure 8:
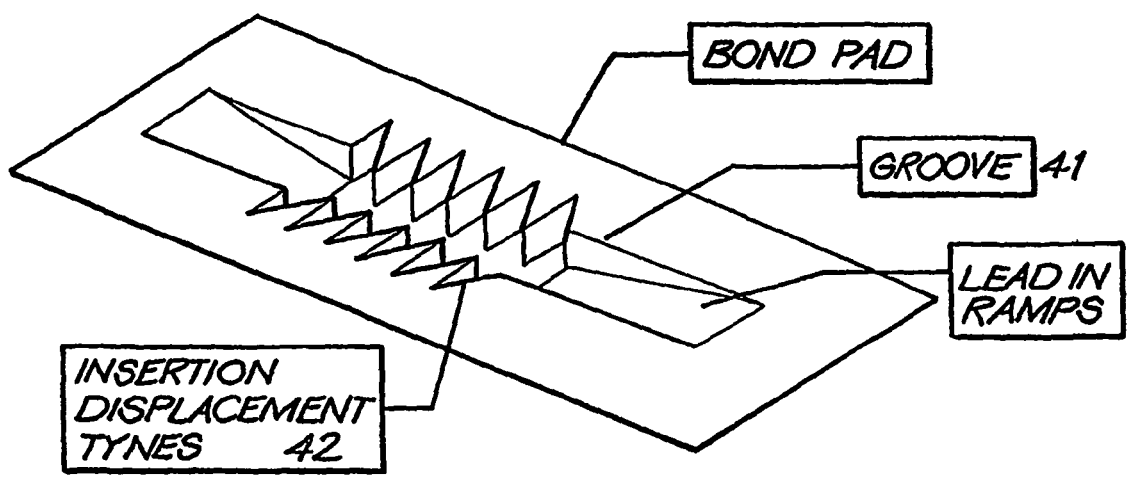
FIG. 8 is a perspective view of one example of a bond pad for use in the present invention.

In still another arrangement and as depicted in FIG. 8, the input pads 18 can be fabricated to form insertion displacement connectors. The connector can be fabricated by micromachining a cavity 41 having a plurality of sharp tines 42 formed in the surface thereof (see FIG. 8). On pushing the wire 13 into this cavity 41, the sharp tines 42 pierce the insulation of the wire 13 and so make electrical connection with the wire 13.

The carrier 20 is formed by molding a suitable biocompatible polymer around the wires 13, circuitry 10 and electrodes 11.

The carrier 20 has a first substantially straight configuration selected to allow it to be inserted into an implantee's body and at least a second spirally curved configuration wherein the carrier is adapted to apply a preselected tissue stimulation with the electrodes 11.

A stiffening element having a configuration selected for biasing the carrier member into the first configuration can pass through at least a portion of the carrier member. The stiffening element can be a metallic stylet disposed in a lumen 51 passing through the carrier 20.

In the depicted embodiment, the carrier 20 is formed from a suitable biocompatible silicone, such as Silastic MDX 4-4210. In another embodiment, the carrier 20 can be formed from a polyurethane.

Figure 6:
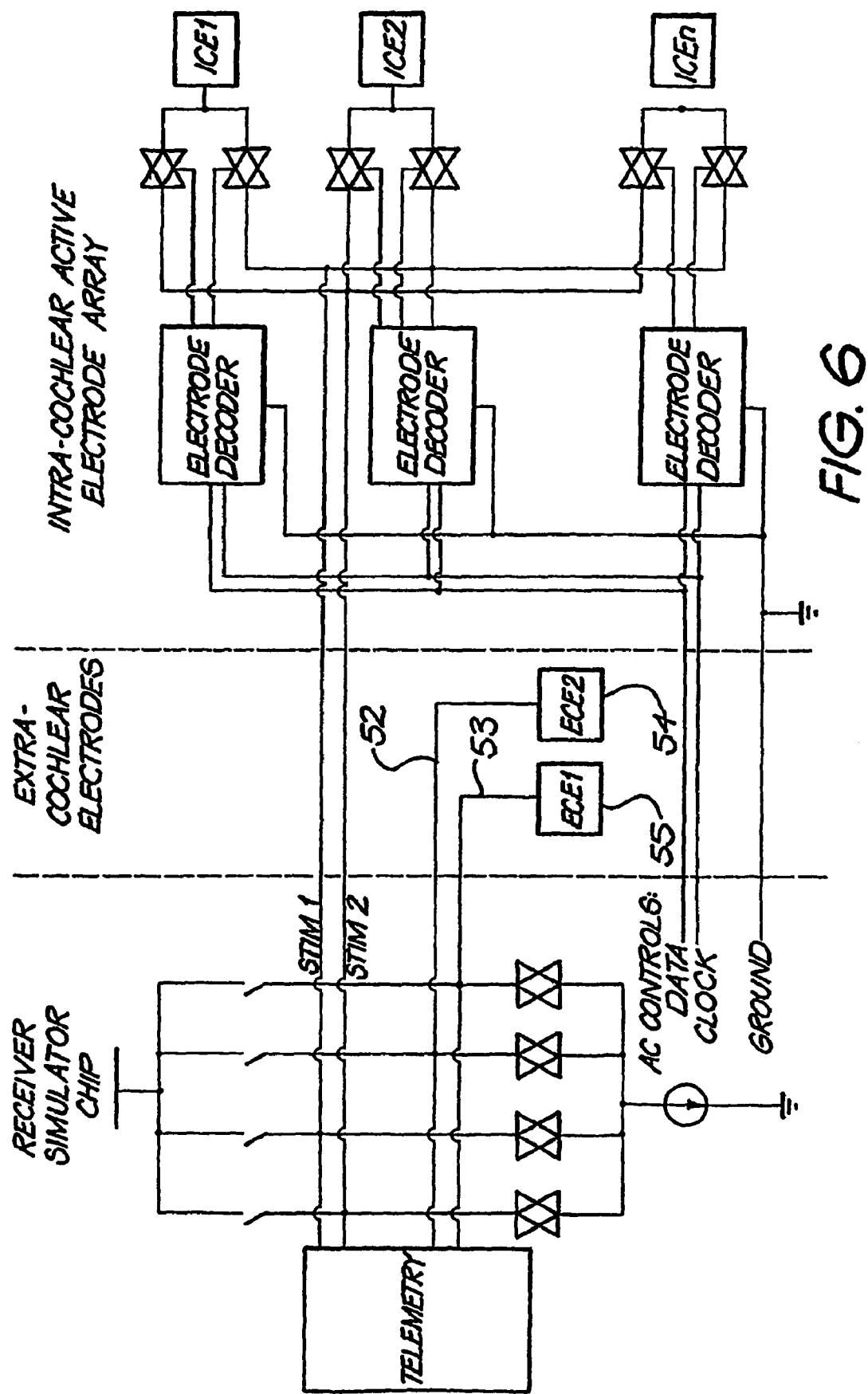
FIG. 6 is a schematic diagram of the stimulation/telemetry system used in the circuitry of the present invention.

In the depicted embodiment, the receiver/stimulator 22 of the cochlear implant is electrically connected to the data line 13b and the clock line 13a. It is also electrically connected and drives four output stimulation lines. As depicted in FIG. 6, two of these lines 52,53 are connected to two extra-cochlear electrodes 54,55. The other two lines, hereinafter called "stim 1" and "stim 2", extend through the carrier member and are connected to the respective input pads of the embedded circuits.

Each of the four lines can be connected, under the control of the receiver/stimulator circuit, to either VDD or to an on-chip stimulus current source.

The stimulation charge, delivered to the cochlea, is, in the depicted embodiment, balanced by using a two-phase balanced stimulation scheme. During the first phase, the active electrode 11 is connected to the current source while the reference electrode is connected to VDD. This allows the current to flow from the reference electrode, through the cochlea and other tissue, to the active electrode 11. During the second phase, the electrode connections are reversed allowing equal, but opposite polarity, charge to flow through the cochlea. This preferably results in a balanced (zero average) charge flow through the stimulating electrodes and the human tissue.

Despite the above, precise charge balance may not be achievable in practice due to small timing errors or variation in electrode properties. To overcome this problem, the output transmission gates (switches) 17 can be closed after the second stimulation phase, thereby connecting all intra-cochlea electrodes 11 to stim 1 and stim 2 simultaneously. These electrodes 11 can be connected to VDD via the output switches of the receiver/stimulator circuit 22. Depending on the desired shorting scheme, the extra-cochlear electrodes 54,55 may also be shorted to VDD together with the intracochlea electrodes 11 in order to simultaneously discharge any residual charge on all electrodes 11. The insertion of series capacitors with some, or all, of the four output lines of the receiver/stimulator circuit serves to ensure the longer term charge balance of the system.

As discussed, the implant is preferably capable of three stimulation modes. Monopolar stimulation is obtained by selecting an extra-cochlear electrode, and an intra-cochlear electrode as the stimulating electrodes. In this mode, the post-stimulating shorting must involve the extra-cochlea electrodes.

The bipolar stimulation is preferably achieved by selecting two intra-cochlear electrodes as the stimulating electrodes. The post-stimulation shorting, in this case, does not need to involve the extra-cochlear electrodes.

The Common Ground stimulation is obtained by selecting an intra-cochlea electrode as an active electrode (connected to stim 1), while all other intra-cochlea electrodes are connected in parallel to stim 2 by simultaneously closing their output switches (transmission gates) during the stimulus phases.

A telemetry circuit can reside in the receiver/stimulator circuit 22 and be connected to the four output lines. This enables the telemetry circuit to measure the voltage of any of the four lines with respect to an internal reference, or differentially between any two of the four lines.

Three telemetry functions are available when using the system, namely Current Source Voltage Compliance Telemetry, Voltage Telemetry, and Neural Response Telemetry.

Current Source Voltage Compliance Telemetry is used to measure the voltage across the stimulation current source of the receiver/stimulator circuit. This telemetry function returns one of two states indicating the voltage across the current source during stimulation. If the measured voltage falls below a design threshold, it may not then be sufficient to maintain the correct operation of the current source. This telemetry function is available for both monopolar and bipolar stimulation modes.

Electrode Voltage Telemetry is used to measure the voltage of an intra-cochlea electrode during stimulation. When voltage telemetry is used to measure the voltage of the active electrode, it can then be used with either monopolar or bipolar stimulation modes. However, only monopolar stimulation can facilitate using Voltage telemetry to measure the voltage of a non-stimulating intra-cochlea electrode, where one of the two lines, stim 1 and stim 2, is used to carry the monopolar stimulation current while the other is used as a sense line to connect to the electrode to be measured.

Neural Response Telemetry can be used to measure the evoked potential of the auditory nerve after stimulation. This is achieved in the monopolar mode by using either stim 1 or stim 2 as a sense line for the neural response electrode. To reduce the stimulation artifacts, one of the extra-cochlea electrodes can be used as a stimulation reference electrode, while the other can be used as a reference electrode for the neural response measurement.

Figure 7:
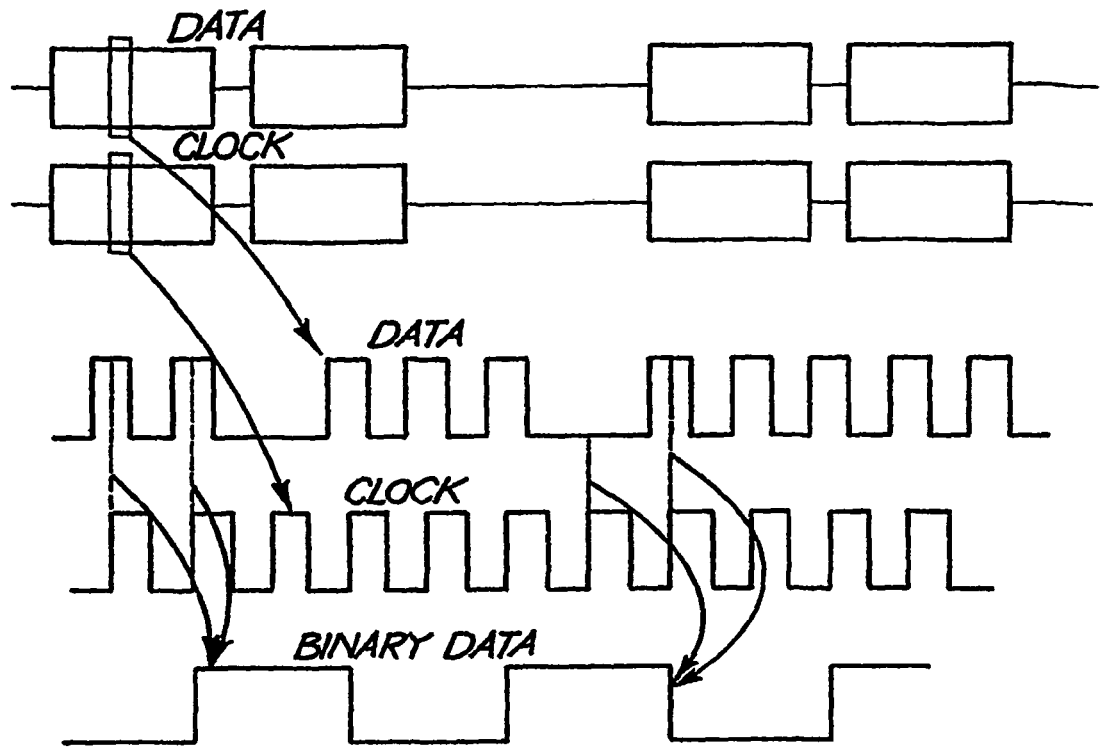
FIG. 7 is one example of a possible data protocol for use in the present invention.

One possible data protocol for use with the present invention is depicted in FIG. 7. This data protocol is based on modulating the signal on the data line 13b with the stimulus and telemetry data. Binary data is represented by a sequence of data pulses. A binary data 1 is represented by two successive data pulses. A missing data pulse followed by a data pulse represents a binary zero. The clock signal, however, has all its pulses existing, with the rising edges delayed with respect to the rising edges of the data pulses. The leading edge of the clock pulses are used to latch the data into a shift register. Depending on the stored pattern, the data in the shift register is decoded into binary ones or zeros as depicted in FIG. 7. The binary data is further decoded to extract the stimulation and telemetry functions to be executed on the next stimulation frame.

In the case where the carrier 20 has 64 electrodes 11, the binary data is used to select the following:
- the active electrode (64 choices, i.e. 6 bits)
- the reference electrode (64 choices, i.e. 6 bits)
- stimulation mode (3 choices, 2 bits)
- telemetry sense electrode (64 choices, 6 bits)
- telemetry modes (3 choices, 2 bits)
- synchronization sequence (4 bits).

This adds up to a total of 26 bits of binary data, which will be transmitted over one stimulus frame (2 phases). If a 2 MHz carrier is used, the minimum phase length needs to be 13 µs. Assuming that the inter-frame gap and the inter-phase gap are 5 µs each, the stimulus frame is 36 µs. This is a stimulation frame of 27777 frames per second. Faster stimulation rates can be achieved by either using a higher clock frequency, or by limiting the stimulation and telemetry modes to the most practically used modes.

The most significant advantage of the present invention is that only a relatively small number of wires 13 need to extend through the carrier 20. By reducing the number of wires 13, the cross-sectional area of the carrier 20 is reduced.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An implantable tissue-stimulating component of an implantable auditory prosthesis comprising:
   a carrier member;
   a plurality of stimulation sites disposed in an array along at least a portion of the carrier member; and
   a plurality of signal transmitting means extending through the carrier member, wherein the number of the signal transmitting means within the carrier member is less than the number of the stimulation sites, wherein the plurality of the stimulation sites are arranged at individual locations along the plurality of signal transmitting means and each of the stimulation sites comprises a stimulating electrode element and associated electronic circuitry that controls a stimulation output by the stimulating electrode element in response to signals delivered to the stimulation site by the signal transmitting means,
   wherein the plurality of signal transmitting means comprises at least five signal transmitting means, the at least five signal transmitting means comprising a clock line, a data line, a first stimulation line, a second stimulation line, and a common ground line.

2. The implantable tissue-stimulating component of claim 1 wherein the component of the implantable auditory prosthesis is in a cochlear implant system.

3. The implantable tissue-stimulating component of claim 1 wherein each said stimulating electrode element has a respective contact face exposed along a first side of the carrier member.

4. The implantable tissue-stimulating component of claim 3 wherein each said contact face is equally spaced from another said contact face along the carrier member.

5. The implantable tissue-stimulating component of claim 1 wherein the stimulating electrode element and the associated circuitry are integrated on a common substrate to form an integrated circuit.

6. The implantable tissue-stimulating component of claim 1 wherein the electronic circuitry comprises a power rectifier, a data decoder, a control circuit, and an output switch.

7. The implantable tissue-stimulating component of claim 6 wherein DC power for the stimulating electrode element is produced by the power rectifier by rectifying an AC power source provided to the power rectifier.

8. The implantable tissue-stimulating component of claim 7 wherein the AC power is provided on two signal transmitting means extending through the carrier member from a receiver/stimulator circuit.

9. The implantable tissue-stimulating component of claim 8 wherein the two signal transmitting means comprise the data line and the clock line.

10. The implantable tissue-stimulating component of claim 9 wherein the data line and clock line are capacitively coupled to the associated electronic circuitry of each of the electrodes in the carrier member using respective input pads.

11. The implantable tissue-stimulating component of claim 6 wherein the data decoder demodulates data and power signals transmitted from a receiver/stimulator circuit, extracts the data and decodes it to obtain stimulation and telemetry control parameters for the stimulating electrode element.

12. The implantable tissue-stimulating component of claim 11 wherein each electrode data decoder determines whether the stimulating electrode element is required to output an electrical stimulation.

13. The implantable tissue-stimulating component of claim 6 wherein the control circuit configures output of the stimulating electrode element in accordance with stimulus and telemetry data decoded by the data decoder.

14. The implantable tissue-stimulating component of claim 6 wherein the output switch directs a stimulation current to a selected said stimulating electrode element and connects a selected stimulating electrode element to a telemetry measurement circuit.

15. The implantable tissue-stimulating component of claim 14 wherein each said output switch also controls a shorting of the stimulating electrode element during an inter-frame period.

16. The implantable tissue-stimulating component of claim 14 wherein each said output switch also opens output of the stimulating electrode element during voltage and neural response telemetry.

17. An implantable tissue-stimulating component of an implantable auditory prosthesis comprising:
   a carrier member;
   a plurality of stimulation sites disposed in an array along at least a portion of the carrier member; and
   a plurality of signal transmitting means extending through the carrier member, wherein the number of the signal transmitting means within the carrier member is less than the number of the stimulation sites; and
   wherein the plurality of the stimulation sites are arranged at individual locations along the plurality of signal transmitting means and each of the stimulation sites comprises a stimulating electrode element and associated electronic circuitry that controls a stimulation output by the stimulating electrode element in response to signals delivered to the stimulation site by the signal transmitting means;
   wherein the plurality of signal transmitting means at least comprise a clock line, a data line, a first stimulation line, a second stimulation line, and a common ground line;
   wherein the electronic circuitry comprises at least a power rectifier, a data decoder, a control circuit, and an output switch;

wherein DC power for the stimulating electrode element is produced by the power rectifier by rectifying an AC power source provided to the power rectifier; and wherein the AC power is provided on two signal transmitting means extending through the carrier member from a receiver/stimulator circuit.

18. An implantable tissue-stimulating component of an implantable auditory prosthesis comprising:

a carrier member;

a plurality of stimulation sites disposed in an array along at least a portion of the carrier member; and a plurality of signal transmitting means extending through the carrier member, wherein the number of the signal transmitting means within the carrier member is less than the number of the stimulation sites; and wherein the plurality of the stimulation sites are arranged at individual locations along the plurality of signal transmitting means and each of the stimulation sites comprises a stimulating electrode element and associated electronic circuitry that controls a stimulation output by the stimulating electrode element in response to signals delivered to the stimulation site by the signal transmitting means;

wherein the plurality of signal transmitting means at least comprise a clock line, a data line, a first stimulation line, a second stimulation line, and a common ground line;

wherein the electronic circuitry comprises at least a power rectifier, a data decoder, a control circuit, and an output switch;

wherein the output switch directs a stimulation current to a selected said stimulating electrode element or connects a selected stimulating electrode element to a telemetry measurement circuit; and wherein each said output switch also opens output of the stimulating electrode element during voltage and neural response telemetry.

19. An implantable tissue-stimulating component of an implantable auditory prosthesis comprising:

a carrier member;

a plurality of stimulation sites disposed in an array along at least a portion of the carrier member; and a plurality of separate electrical leads extending through the carrier member, wherein the number of the electrical leads within the carrier is less than the number of the stimulation sites;

wherein the plurality of the stimulation sites are arranged at individual locations along the plurality of separate electrical leads and the stimulation sites comprise a stimulating electrode element and a respective electronic circuitry assembly configured to control a stimulation output by the respective stimulating electrode element in response to signals delivered to the stimulation site by the electrical leads;

wherein the plurality of electrical leads at least comprise a clock line, a data line, a first stimulation line, a second stimulation line, and a common ground line; and wherein the clock line, the data line, the first stimulation line, the second stimulation line and the common ground line are each electrically connected to the electronic circuitry assemblies.

20. The implantable tissue-stimulating component of claim 19, wherein the electronic circuitry assemblies are configured to demodulate data and power signals transmitted from a receiver/stimulator circuit, extract the data and decode the data to obtain stimulation and telemetry control parameters for the stimulating electrode element.

21. A method of stimulating tissue with an implanted auditory prosthesis, comprising:

delivering a clock signal, a data signal, a first stimulation signal and a second stimulation signal through respective separate electrical leads to a plurality of electronic circuit assemblies respectively in electrical communication with the separate leads, wherein the number of circuit assemblies is greater than the number of electrical leads; and applying separate stimulation outputs to respective tissue locations from respective electrodes in electrical communication with respective electronic circuit assemblies of the plurality of electronic circuit assemblies in response to the signals delivered through the plurality of electrical leads.

22. The method of claim 21, wherein:

the plurality of electronic circuit assemblies are embedded in a carrier of a cochlear implant, and wherein the plurality of electrical leads extend from a stimulator unit of the cochlear implant.

23. The implantable tissue-stimulating component of claim 1 wherein the clock line, the data line, the first stimulation line, the second stimulation line and the common ground line are separate from each other.

24. The implantable tissue-stimulating component of claim 17 wherein the clock line, the data line, the first stimulation line, the second stimulation line and the common ground line are separate from each other.

25. The implantable tissue-stimulating component of claim 18 wherein the clock line, the data line, the first stimulation line, the second stimulation line and the common ground line are separate from each other.

* * * * *